(12) United States Patent
Pluta

(10) Patent No.: US 12,313,620 B2
(45) Date of Patent: May 27, 2025

(54) SIGNAL-BASED MEDIUM ANALYSIS

(71) Applicant: Blue Lab Solutions, LLC, Scotia, NY (US)

(72) Inventor: Sarah E. Pluta, Scotia, NY (US)

(73) Assignee: Blue Lab Solutions, LLC, Scotia, NY (US)

( * ) Notice: Subject to any disclaimer, the term of this patent is extended or adjusted under 35 U.S.C. 154(b) by 172 days.

(21) Appl. No.: 18/121,079

(22) Filed: Mar. 14, 2023

(65) Prior Publication Data

US 2023/0213495 A1 Jul. 6, 2023

Related U.S. Application Data

(63) Continuation of application No. 17/567,797, filed on Jan. 3, 2022, now Pat. No. 11,635,420, which is a continuation of application No. 16/652,237, filed as application No. PCT/US2018/054316 on Oct. 4, 2018, now Pat. No. 11,215,602.

(Continued)

(51) Int. Cl.
| | |
|---|---|
| *G01N 27/02* | (2006.01) |
| *G01N 33/24* | (2006.01) |
| *G01V 3/08* | (2006.01) |
| *G01V 3/15* | (2006.01) |

(52) U.S. Cl.
CPC ......... *G01N 33/246* (2013.01); *G01N 27/026* (2013.01); *G01V 3/088* (2013.01); *G01V 3/15* (2013.01); *G01N 33/245* (2024.05)

(58) Field of Classification Search
CPC .... G01N 33/246; G01N 27/026; G01V 3/088; G01V 3/15
See application file for complete search history.

(56) References Cited

U.S. PATENT DOCUMENTS 5,811,973 A * 9/1998 Meyer, Jr. ................ G01V 3/30
324/338
6,484,652 B1 11/2002 Colburn, Jr.
(Continued)

FOREIGN PATENT DOCUMENTS

| KR | 20060132329 A | 12/2006 |
| WO | 2019215257 A2 | 11/2019 |

OTHER PUBLICATIONS

CA Application No. 3,115,858, Office Action dated Feb. 2, 2024, 6 pages.

(Continued)

*Primary Examiner* — Dominic E Hawkins
(74) *Attorney, Agent, or Firm* — LaBatt, LLC

(57) ABSTRACT

A solution for evaluating a medium using electrical signals is described. A plurality of electrical signals having different frequencies are transmitted through the medium and signal data corresponding to the electrical signals after having traveled through the medium is acquired. A complex impedance and a complex permittivity and/or complex conductivity can be calculated for the medium. A set of characteristics of the medium can be computed using mixing models and/or known information of the medium. A level of one or more attributes of the medium can be determined from the characteristics using nonparametric Bayesian inference. One particular application is directed to determining a nitrate level of soil.

20 Claims, 4 Drawing Sheets

Related U.S. Application Data

(60) Provisional application No. 62/567,885, filed on Oct. 4, 2017.

(56) References Cited

U.S. PATENT DOCUMENTS

| | | | |
|---|---|---|---|
| 7,408,364 | B1 | 8/2008 | Campbell |
| 7,508,221 | B2 | 3/2009 | Wuersch et al. |
| 7,705,614 | B2 | 4/2010 | Troxler et al. |
| 8,947,102 | B1 | 2/2015 | Evett et al. |
| 9,146,223 | B1 | 9/2015 | Gerber-Siff et al. |
| 10,073,074 | B1 | 9/2018 | Kumar et al. |
| 2004/0145379 | A1* | 7/2004 | Buss ............... G01N 27/223 |
| | | | 324/664 |
| 2005/0267700 | A1 | 12/2005 | Gamache et al. |
| 2009/0270756 | A1 | 10/2009 | Gamache et al. |
| 2010/0134114 | A1 | 6/2010 | Hwang |
| 2012/0130212 | A1 | 5/2012 | Pluta et al. |
| 2013/0307564 | A1 | 11/2013 | Colosimo et al. |
| 2014/0347056 | A1 | 11/2014 | Hayman et al. |
| 2015/0087072 | A1 | 3/2015 | Adamchuk et al. |
| 2015/0137831 | A1 | 5/2015 | Pluta et al. |
| 2015/0212026 | A1 | 7/2015 | Pluta et al. |
| 2016/0054247 | A1 | 2/2016 | Colosimo et al. |
| 2016/0161624 | A1 | 6/2016 | Pluta et al. |
| 2016/0313443 | A1 | 10/2016 | Al-Shuhail et al. |
| 2017/0199140 | A1 | 7/2017 | Colosimo et al. |
| 2018/0011039 | A1 | 1/2018 | Colosimo et al. |
| 2018/0164466 | A1 | 6/2018 | Zhang |
| 2018/0239044 | A1* | 8/2018 | Rhodes ............... G01N 33/246 |
| 2021/0223226 | A1 | 7/2021 | Grabbert et al. |

OTHER PUBLICATIONS

Office Action for EP Application No. 18793533.3-1020, mailed Jun. 6, 2023, 7 pages.
Veronesi, Fabio, "Linear Mixed Effects Models in Agriculture | R-bloggers," Jul. 10, 2017, Retrieved from https://www.r-bloggers.com/linear-mixed-effects-models-in-agriculture/ on Dec. 6, 2018, 5 pages.
De Masi, Rita, International Search Report and Written Opinion for PCT/US2018/054316, Dec. 20, 2018, 15 pages.
Hawkins, Dominic E., U.S. Appl. No. 16/652,237, Notice of Allowance, Aug. 20, 2021, 10 pages.
Hawkins, Dominic E., U.S. Appl. No. 16/652,237, Office Action 1, Mar. 30, 2021, 16 pages.
De Masi, Rita, EP Application No. 18793533.3-1020, Office Action 1, Oct. 19, 2021, 4 pages.
Hawkins, Dominic E., U.S. Appl. No. 17/567,797, Notice of Allowance, Dec. 12, 2022, 9 pages.
Office Action for Canadian Patent Application No. 3, 115,858, Dec. 10, 2024, 4 pages.

* cited by examiner

SIGNAL-BASED MEDIUM ANALYSIS

REFERENCE TO RELATED APPLICATIONS

The current application is a continuation of U.S. patent application Ser. No. 17/567,797, filed on 3 Jan. 2022, which is a continuation of U.S. patent application Ser. No. 16/652,237, filed on 30 Mar. 2020, which is a U.S. National Phase application of International Application No. PCT/US2018/054316, filed on 4 Oct. 2018, which claims the benefit of U.S. Provisional Application No. 62/567,885, filed on 4 Oct. 2017, all of which are hereby incorporated by reference.

TECHNICAL FIELD

The disclosure relates generally to analysis of a medium using electrical signals, and more particularly, to a solution for measuring various characteristics of the medium from signal data for multiple frequencies transmitted through the medium.

BACKGROUND ART

There are numerous economic and environmental issues related to soil and water management. A broad societal economic issue is that as the population continues to increase, crop yield becomes more important. For instance, from 1962 to 2000, the amount of land used around the world for crop production increased by 13%, while the world population increased by 89%.

These issues increase the need to better understand the role of particular nutrients, such as nitrogen, in crop production. Nitrogen rich fertilizer has contributed an estimated 40% to the increase in per-capita food production in the past 50 years. In addition, the productivity and efficiency of the land and a crop's growth and quality have a direct relationship to the cost of those goods to the consumer, even if the full effect takes 10 to 12 months to move through the retail food chain.

Profitability of farmed crops can be severely negatively impacted if poor nitrogen management practices are used. One of the limitations is the inability to assess soil and plant data rapidly and inexpensively in the field. A key component and barrier is the lack of a soil nitrate-nitrogen measurement system. Hence, much research continues to focus on the development of instrumentation to help in the precision agriculture (PA) decision-making process by measuring different soil attributes within a field.

Soil nitrogen is often deficient, despite the fact that it is an essential nutrient for optimal crop production. When soil nitrogen is too abundant and exceeds a crop's requirements, there is a greater likelihood of negative environmental impacts such as leaching, denitrification, and volatilization. Nitrogen in the soil also can be lost through crop removal, soil erosion, and runoff. By monitoring important soil characteristics (e.g., nitrate levels and moisture) in multiple locations over a field of interest, the development of a water and fertilizer plan can be adapted more easily to changing environmental conditions and crop needs. This effort results in substantial positive environmental and economic returns for farmers.

The amount of fertilizer necessary varies with the crop to be grown, the desired yield, the amount of nutrients (e.g., nitrogen) already present in the soil, and the region in which the crops are grown. Therefore, it is common practice to base fertilizer application amounts on local knowledge and expertise. For corn, it is common to measure the soil nitrates using a Pre-sidedress Nitrate Test (PSNT), which is an in-season soil nitrate test that is done to determine if additional nitrogen rich fertilizer is needed to reach optimal yield. To complete this test, 12-inch soil cores are taken from the field, usually one or two cores per acre due to the time and effort involved. The soil samples are processed quickly to stop the microbe activity and the composite field sample is mailed to a laboratory to measure the nitrate level using a spectrophotometric meter. The sampling, processing, mailing, and analyzing process may take 48 hours. If a field soil test kit with a commercial handheld meter or test strips is used, the sampling, processing, and testing still can take 24 hours.

Depending on the relative uniformity of the field with respect to soil characteristic, different corn strands, management history, etc., the sample area size can vary from 1 to 10 acres or more. In other soil sampling strategies, it is common to collect 15 to 30 soil cores at depths varying from six inches to two feet to represent 10 to 20 acres, assuming a uniform field. As with the PSNT, the samples need to be processed for the nitrate measurement with the same labor intensive and time-consuming efforts.

SUMMARY OF THE INVENTION

Aspects of the invention provide a solution for evaluating a medium using electrical signals. A plurality of electrical signals having different frequencies are transmitted through the medium and signal data corresponding to the electrical signals after having traveled through the medium is acquired. A complex impedance and a complex permittivity and/or a complex conductivity can be calculated for the medium. A set of characteristics of the medium can be computed using mixing models and/or known information of the medium. A level of one or more attributes of the medium can be determined from the characteristics using nonparametric Bayesian inference.

One illustrative application is directed to determining a nitrate level of soil. To this extent, an embodiment provides a field in-situ instrument that can measure soil nutrient content, such as a nitrate concentration, in real-time. The results provided by the instrument can aid in the decision-making process for developing an effective crop growth strategy. Additionally, the instrument can add to the collection of tools used in precision agriculture (PA), where optimizing returns while preserving resources is an important goal. To this extent, the instrument can help improve agricultural soil health, thereby improving an effectiveness of farmers and agriculture professionals with their land and other resources, while maintaining optimum crop yield and production efficiency. Providing real-time information can allow for field plans to be developed or adapted to conditions more quickly and easily by farmers and land managers. In addition, such information can provide an easier way to do more localized testing of soil conditions with greater ease, thereby further reducing the negative environmental and economic effects of harmful and damaging over fertilization.

A first aspect of the invention provides a system comprising: a computer system including means for evaluating a medium, the means for evaluating including: obtaining signal data corresponding to a plurality of electrical signals having traveled through the medium, each of the plurality of electrical signals having a different frequency; measuring a complex impedance of the medium using the signal data; computing at least one of: a complex permittivity or a complex conductivity, using the complex impedance and an electrode model corresponding to a configuration of electrodes used to acquire the signal data; computing a set of characteristics of the medium using the at least one of: the complex permittivity or the complex conductivity, and a set of mixing models, wherein each characteristic in the set of characteristics has at least one corresponding mixing model in the set of mixing models; and providing the set of characteristics for use in evaluating the medium.

An embodiment of the system can include a conducting electrode for transmitting the electrical signals and a set of probe electrodes for acquiring the signal data corresponding to the electrical signals after passing through the medium. The computer system can operate the conducting electrode to transmit each of the signals into the medium and receive the signal data from the set of probe electrodes located in the medium. In a more particular embodiment, each probe electrode includes a pair of guard electrodes located on opposing sides of a guarded electrode. An embodiment of the set of probe electrodes can include at least two probe electrodes, with each of the probe electrodes located a known distance from the conducting electrode and at a known position relative to each of the other probe electrodes.

The computer system can obtain known information regarding the medium from one or more sources of information, such as a user, a previous test, an external data source, etc. The known information can be used in one or more of various stages of processing the signal data. For example, known information can be used in conjunction with a set of characteristics for the medium to determine at least one attribute level.

The computer system can implement various models and approaches for determining the characteristic(s) and/or attribute level(s) of the medium. The computer system can use an electrode model to remove an effect of the electrode configuration from the signal data. An embodiment of the electrode model corresponds to a transmission line model. One or more attribute levels of the medium can be determined using a nonparametric Bayesian inference solution.

In an illustrative embodiment described herein, the medium comprises soil, such as agricultural soil. An embodiment of a system can provide a portable solution for evaluating the soil in situ and obtaining measurements of one or more characteristics of the soil and/or attribute levels of the soil in real time. The characteristics can include a water content of the soil and an attribute level can include a nitrate level of the soil. The results of the evaluation can be provided for use in managing one or more aspects of the soil, such as determining and/or modifying a watering schedule, a fertilization schedule, etc.

A second aspect of the invention provides a method of evaluating a medium, the method comprising: obtaining signal data corresponding to a plurality of electrical signals having traveled through the medium on a computer system, each of the plurality of electrical signals having a different frequency; the computer system measuring a complex impedance of the medium using the signal data; the computer system computing at least one of: a complex permittivity or a complex conductivity, using the complex impedance and an electrode model corresponding to a configuration of electrodes used to acquire the signal data; the computer system computing a set of characteristics of the medium using the at least one of: the complex permittivity or the complex conductivity, and a set of mixing models, wherein each characteristic in the set of characteristics has at least one corresponding mixing model in the set of mixing models; and the computer system providing the set of characteristics for use in evaluating the medium.

A third aspect of the invention provides a portable soil evaluation system comprising: an electrode component including: a conducting electrode for transmitting a plurality of electrical signals; and a set of probe electrodes for acquiring signal data corresponding to the plurality of electrical signals after passing through soil; and a computer system including means for evaluating the soil, the means for evaluating including: operating the electrode component to emit a plurality of electrical signals from the conducting electrode and acquire signal data from at least one of the set of probe electrodes corresponding to the plurality of electrical signals having traveled through the soil, each of the plurality of electrical signals having a different frequency; measuring a complex impedance of the soil using the signal data; computing at least one of: a complex permittivity or a complex conductivity, using the complex impedance and an electrode model corresponding to a configuration of the conducting electrode and the set of probe electrodes used to acquire the signal data; computing a set of characteristics of the medium using the at least one of: the complex permittivity or the complex conductivity, and a set of mixing models, wherein each characteristic in the set of characteristics has at least one corresponding mixing model in the set of mixing models; determining at least one attribute level in the soil using known information of the soil and at least one of the set of characteristics for the soil; and presenting the at least one attribute level to the user in real time.

The illustrative aspects of the invention are designed to solve one or more of the problems herein described and/or one or more other problems not discussed.

BRIEF DESCRIPTION OF THE DRAWINGS

These and other features of the disclosure will be more readily understood from the following detailed description of the various aspects of the invention taken in conjunction with the accompanying drawings that depict various aspects of the invention.

It is noted that the drawings may not be to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

Aspects of the invention provide a solution for evaluating a medium using electrical signals. A plurality of electrical signals having different frequencies are transmitted through the medium and signal data corresponding to the electrical signals after having traveled through the medium is acquired. A complex impedance and a complex permittivity and/or complex conductivity can be calculated for the medium. A set of characteristics of the medium can be computed using mixing models and/or known information of the medium. A level of one or more attributes of the medium can be determined from the characteristics using nonparametric Bayesian inference.

In an illustrative application of the invention used to illustrate various aspects of the invention, a solution for analyzing one or more aspects of soil nutrient content is described. Embodiments can perform the analysis of the soil in-situ, thereby not requiring the acquisition and processing of soil samples for testing. In an illustrative embodiment, a solution for analyzing the nitrate concentration in agricultural soil is described. However, it is understood that nitrate concentration is only illustrative of the soil nutrient analysis that can be performed in embodiments. Additionally, agricultural soil is also only illustrative of the types of soil that can be analyzed using a solution described herein. Still further, soil is only illustrative of various types of media that can be analyzed using a solution described herein.

Figure 1:
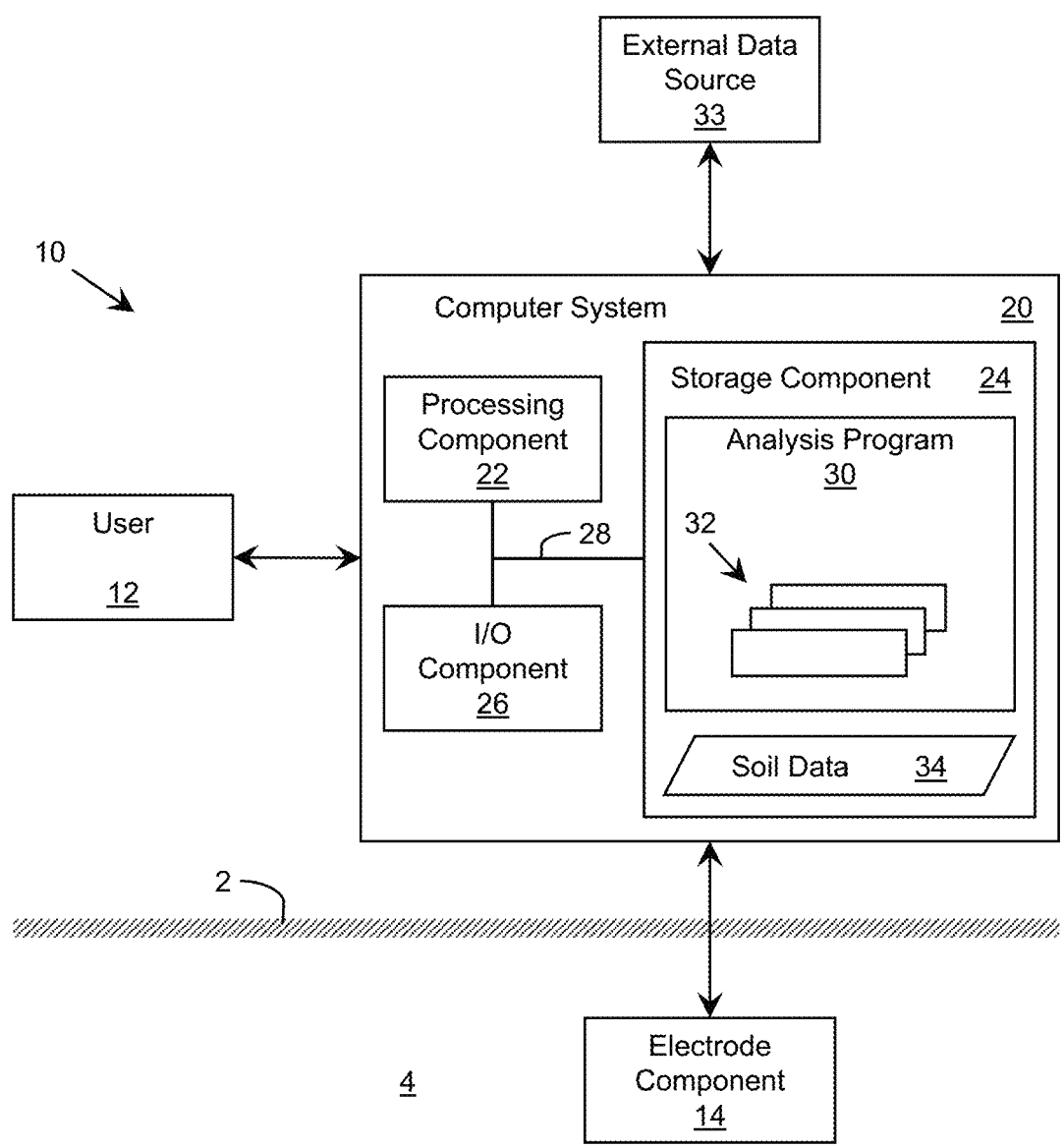
FIG. 1 shows an illustrative environment for analyzing soil according to an embodiment.

Turning to the drawings, FIG. 1 shows an illustrative environment 10 for analyzing soil according to an embodiment. To this extent, the environment 10 includes a computer system 20 that can perform a process described herein in order to analyze one or more aspects of soil 4. In particular, the computer system 20 is shown including an analysis program 30, which makes the computer system 20 operable to analyze the soil 4 by performing a process described herein.

The computer system 20 is shown including a processing component 22 (e.g., one or more processors), a storage component 24 (e.g., a storage hierarchy), an input/output (I/O) component 26 (e.g., one or more I/O interfaces and/or devices), and a communications pathway 28. In general, the processing component 22 executes program code, such as the analysis program 30, which is at least partially fixed in storage component 24. While executing program code, the processing component 22 can process data, which can result in reading and/or writing transformed data from/to the storage component 24 and/or the I/O component 26 for further processing. The pathway 28 provides a communications link between each of the components in the computer system 20.

The I/O component 26 can enable the computer system 20 to communicate directly with a human and/or one or more other components or systems. To this extent, the I/O component 26 can comprise one or more human I/O devices, which enable a human user 12 to interact with the computer system 20 and/or one or more communications devices to enable a system user 12, another component of the system (e.g., an electrode component 14), an external data source 33, and/or the like, to communicate with the computer system 20 using any combination of one or more of various types of communications links. To this extent, the analysis program 30 can manage a set of interfaces (e.g., graphical user interface(s), application program interface, and/or the like) that enable human and/or system users 12 to interact with the computer system 20. Furthermore, the analysis program 30 can manage (e.g., store, retrieve, create, manipulate, organize, present, etc.) the data, such as soil data 34, using any solution.

In any event, the computer system 20 can comprise one or more general purpose computing articles of manufacture (e.g., computing devices) capable of executing program code, such as the analysis program 30, installed thereon. As used herein, it is understood that "program code" means any collection of instructions, in any language, code or notation, that cause a computing device having an information processing capability to perform a particular action either directly or after any combination of the following: (a) conversion to another language, code or notation; (b) reproduction in a different material form; and/or (c) decompression. To this extent, the analysis program 30 can be embodied as any combination of system software and/or application software.

Furthermore, the analysis program 30 can be implemented using a set of modules 32. In this case, a module 32 can enable the computer system 20 to perform a set of tasks used by the analysis program 30, and can be separately developed and/or implemented apart from other portions of the analysis program 30. As used herein, the term "component" means any configuration of hardware, with or without software, which implements the functionality described in conjunction therewith using any solution, while the term "module" means program code that enables a computer system 20 to implement the actions described in conjunction therewith using any solution. When fixed in a storage component 24 of a computer system 20 that includes a processing component 22, a module is a substantial portion of a component that implements the actions. Regardless, it is understood that two or more components, modules, and/or systems may share some/all of their respective hardware and/or software. Furthermore, it is understood that some of the functionality discussed herein may not be implemented or additional functionality may be included as part of the computer system 20.

When the computer system 20 comprises multiple computing devices, each computing device can have only a portion of the analysis program 30 fixed thereon (e.g., one or more modules 32). However, it is understood that the computer system 20 and the analysis program 30 are only representative of various possible equivalent computer systems that may perform a process described herein. To this extent, in other embodiments, the functionality provided by the computer system 20 and the analysis program 30 can be at least partially implemented by one or more computing devices that include any combination of general and/or specific purpose hardware with or without program code. In each embodiment, the hardware and program code, if included, can be created using standard engineering and programming techniques, respectively.

Regardless, when the computer system 20 includes multiple computing devices, the computing devices can communicate over any type of communications link. Furthermore, while performing a process described herein, the computer system 20 can communicate with one or more other computer systems and/or components (such as the electrode component 14 and/or the external data source 33) of a system described herein using any type of communications link. In either case, the communications link can comprise any combination of various types of optical fiber, wired, and/or wireless links; comprise any combination of one or more types of networks; and/or utilize any combination of various types of transmission techniques and protocols.

As discussed herein, the analysis program 30 enables the computer system 20 to analyze a medium, such as soil 4. To this extent, the computer system 20 can receive soil data 34 from a electrode component 14 which is located at a desired location below ground 2, in the soil 4. The computer system 20 (e.g., as directed by the analysis program 30) can operate the electrode component 14 and/or process the soil data 34 and generate additional soil data 34 therefrom. The computer system 20 can evaluate the additional soil data 34 to determine one or more characteristics and/or attributes of interest of the soil. The computer system 20 also can obtain data relevant to the evaluation from one or more external data sources 33. Illustrative external data sources 33 can include a soil management system used to manage the soil 4, a government database, and/or the like. Information that can be obtained from the external data source(s) 33 can include data corresponding to: a previous evaluation of the soil 4; a previous treatment applied to the soil 4; recent weather for an area in which the soil 4 is located; soil survey information; etc.

In an embodiment, the environment 10 is configured to provide a portable solution for analyzing one or more attributes of the soil 4 in real time. To this extent, the computer system 20 and the electrode component 14 can be configured to be portable by a single person, rugged, and easy to use. The electrode component 14 can include electrodes, which can be individually replaced should one become damaged, or in the event that a different depth of measurement is desired. The electrode component 14 can be configured to facilitate locating multiple electrodes in the soil 4 with a known arrangement. For example, the electrode component 14 can include a conducting electrode and one or more probe electrodes. The electrode component 14 can enable placement of the electrodes in the soil 4 such that each probe electrode is a known distance from the conducting electrode and is located at a known position relative to each of the other probe electrode(s). As used herein, a distance is known when it is sufficiently accurate for the corresponding calculations to have a desired accuracy. In a more particular embodiment, the distance is accurate to within +/−5 millimeters. Additionally, as used herein a relative position of two probe electrodes is known when an angle formed by the two probe electrodes with the conducting electrode at a vertex is known to an accuracy sufficient for the corresponding calculations to have a desired accuracy. In a more particular embodiment, the angle is accurate to within +/−5 degrees.

Figure 2A:
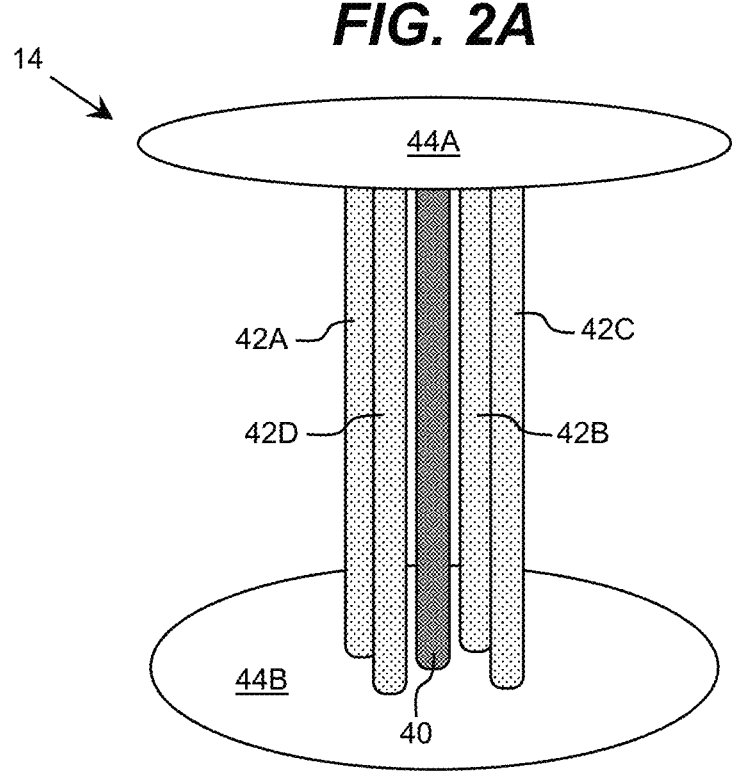
FIGS. 2A and 2B show perspective and top views, respectively, of an illustrative electrode component according to an embodiment.
Figure 2B:
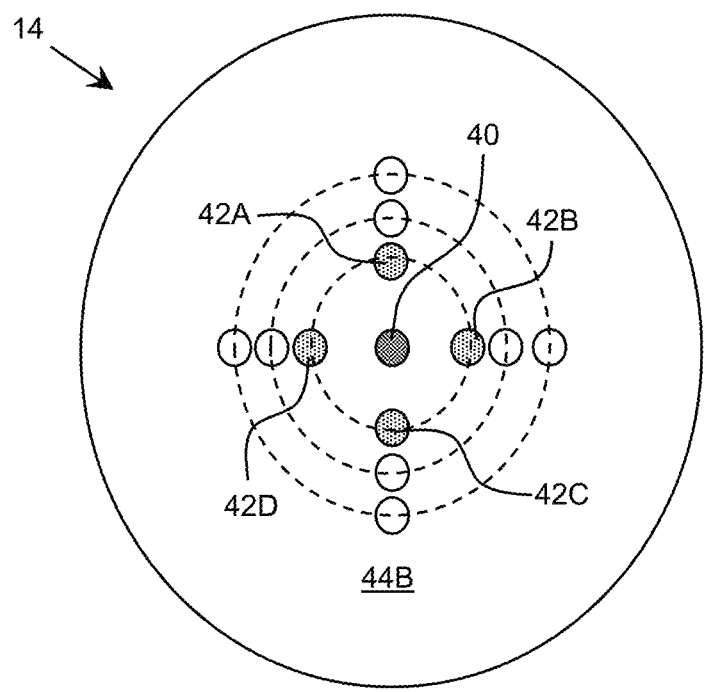

FIGS. 2A and 2B show perspective and top views, respectively, of an illustrative electrode component 14 according to an embodiment. In this case, the electrode component 14 comprises five electrode structures 40, 42A-42D. A conducting electrode structure 40 can be surrounded by four probe electrode structures 42A, 42D, each of which can be located at substantially the same distance from the conducting electrode structure 40 and spaced evenly (e.g., arranged 90°) from each other. As illustrated in FIG. 2B, the actual distance between the conducting electrode structure 40 and each of the probe electrode structures 42A-42D can vary. For example, the electrode component 14 can be pre-configured and/or include a template or guide that enables a user to selectively install the probe electrode structures 42A-42D at any of a plurality of distances from the conducting electrode structure 40. Regardless, it is understood that the distance must be known so that proper calculations can be performed as described herein.

While all of the probe electrode structures 42A-42D are shown as being located the same distance from the conducting electrode structure 40, it is understood that this configuration is only illustrative. In an embodiment, the distances between the conducting electrode structure 40 and the probe electrode structures 42A-42D vary. Regardless, the distance between each probe electrode structure 42A-42D and the conducting electrode structure 40 must be known to an accuracy sufficient for the models. In an embodiment, the computer system 20 (FIG. 1) can specify a configuration for placement of the probe electrode structures 42A-42D based on one or more prior known conditions of the soil. For example, the computer system 20 can specify that two probe electrodes (e.g., located across from each other) be located at a first distance from the conducting electrode structure 40 while two probe electrodes are specified to be located at a second, different distance from the conducting electrode structure 40. The distance(s) between the conducting electrode structure 40 and each of the probe electrode structures 42A-42D can be in any range of distances. In an embodiment, the distance(s) are at least 20 millimeters. In a more particular embodiment, the distances are in a range between 20 millimeters and 20 centimeters.

An embodiment of the electrode component 14 can include one or more components to facilitate proper and accurate placement of the electrode structures 40, 42A-42D within the soil. In an embodiment, the electrode component 14 is configured to secure an end of each of the electrode structures 40, 42A-42D at a particular location and in a particular orientation on a member 44A. For example, the member 44A can include a mechanism for securing an end of each of the electrode structures 40, 42A-42D to the member 44A such that the electrode structures 40, 42A-42D will remain in substantially the same arrangement while the electrode component 14 is inserted into the soil. In an embodiment, the mechanism for an electrode includes a threaded opening in the member 44A into which a threaded end of the electrode can be inserted. In an embodiment, an electrode is connected to the member 44A using a radio frequency connector, such as a Bayonet Neill-Concelman (BNC) connector, which also can connect each electrode structure 40, 42A-42D to the computer system 20.

In an embodiment, the member 44A is configured to secure each electrode structure 40, 42A-42D while allowing the user 12 access to a radio frequency connector for each electrode structure 40, 42A-42D. For example, the connector can be located on a top of each electrode and the member 44A can include an opening that allows access to the connector from a top side of the member 44A. In this configuration, the user 12 can disconnect the electrode structures 40, 42A-42D from the computer system 20 during insertion, removal, and/or transport of the electrode component 14.

In an embodiment, the electrode component 14 can include a template member 44B for facilitating placement of the electrodes in the proper position and/or orientation within the soil. For example, the template member 44B can include openings corresponding to possible configurations for placement of the electrode structures 40, 42A-42D. Each opening can be sized to allow the electrode structure 40, 42A-42D to be inserted there through while also restricting lateral movement of the electrode structure 40, 42A-42D, e.g., due to deflection from the presence of a stone or the like. To this extent, the template member 44B also can have a thickness sufficient to restrict such lateral movement.

Each member 44A, 44B can be formed of any suitable material. For example, the member 44A can be fabricated from a non-conducting material having sufficient strength to allow insertion of the electrode structure 40, 42A-42D into the soil by, for example, pushing down and/or pounding on a top surface of the member 44A without deforming the member 44A. In an embodiment, the electrode structures 40, 42A-42D can be individually inserted into the soil. In this case, the electrode component 14 can be implemented without the member 44A. The member 44B can be used as a template for inserting each electrode structure 40, 42A-42D and can be formed of a material having sufficient strength to withstand inadvertent pounding during insertion of the electrode structures 40, 42A-42D. Use of one or both members 44A, 44B can assist in aligning the electrode structures 40, 42A-42D such that the corresponding electrodes are substantially aligned. Known alignment of the electrodes can reduce errors in the model calculations.

It is understood that insertion of the electrode structures 40, 42A-42D into the soil is only illustrative of various approaches for surrounding the electrode structures 40, 42A-42D with a soil to be tested. For example, in an embodiment, soil can be placed within a container and the electrode component 14 can be inserted therein. Alternatively, the electrode component 14 can comprise a container with the electrode structures 40, 42A-42D mounted therein and the soil can be inserted in the container surrounding the electrodes. Still further, a hole can be dug in the ground into which the electrode component 14 is placed and subsequently surrounded with soil. In this case, one or both members 44A, 44B an include openings (e.g., a screen and/or large scale openings) to allow soil to pass there through and effectively surround the electrode structures 40, 42A-42D. Such placement approaches can be used, for example, when the soil includes a lot of stones, which can preclude accurate placement and orientation of the electrode structures 40, 42A-42D.

Figure 3A:
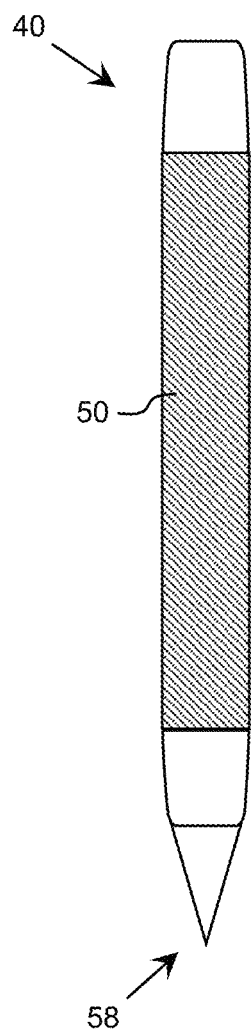
FIGS. 3A and 3B show an illustrative conducting electrode structure and probe electrode structure according to embodiments.
Figure 3B:
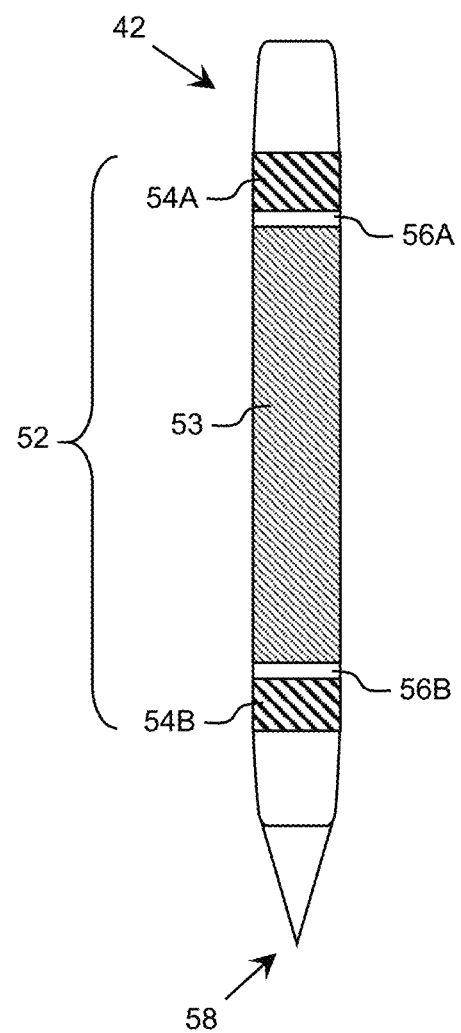

One or more of the electrode structures 40, 42A-42D can be designed and constructed to eliminate electric field fringing effects at the edges of the electrodes. To this extent, FIGS. 3A and 3B show an illustrative conducting electrode structure 40 and probe electrode structure 42 according to embodiments. The conducting electrode structure 40 can comprise a conducting electrode 50, while the probe electrode structure 42 includes a probe electrode 52, which includes guard electrodes 54A, 54B located on opposing sides of a guarded electrode 53. In a more particular embodiment, both electrodes 50, 52 have substantially the same diameters (e.g., approximately 13.7 mm in an illustrative embodiment). The conducting electrode 50 can have a length of approximately 150 mm. The probe electrode 52 also can have an overall length of approximately 150 mm, and include a guarded electrode 53 having a length of approximately 100 mm, with each guard electrode 54A, 54B having a length of approximately 20 mm. A space 56A, 56B can be located between the guarded electrode 53 and each guard electrode 54A, 54B of approximately 5 mm.

It is understood that the various dimensions for the electrodes 50, 52 are only illustrative. To this extent, embodiments of an electrode can have any diameter suitable for use in conjunction with the corresponding model(s) and measurement frequencies. In general, smaller diameters can make insertion of the electrode structures 40, 42 into the soil easier. In an embodiment, the electrodes 50, 52 have diameters in a range between approximately five millimeters and approximately twenty millimeters. Similarly, the heights of the electrodes 50, 52 can be the same or vary. In an embodiment, the electrodes 50, 52 have overall heights in a range between approximately 5 centimeters and 30 centimeters. Furthermore, it is understood that the corresponding electrode structures 40, 42 can have differing dimensions (e.g., diameters and/or heights). Regardless, the dimensions of each electrode 50, 52 must be known to a sufficient accuracy for use in the corresponding model(s).

While only a single probe electrode structure 42 is shown in FIG. 3B, it is understood that each of the probe electrode structures 42A-42D can be constructed in the same manner as the probe electrode structure 42 shown in FIG. 3B. However, it is understood that a probe electrode 52 can be designed and constructed as an unguarded electrode, e.g., similar to the conducting electrode 50. As the electrode structures 40, 42 may be utilized in environments including water, the electrode structures 40, 42 can be constructed to be liquid tight. Additionally, each electrode structure 40, 42 can have a narrowed, pointed end 58 that can facilitate inserting the electrode structure 40, 42 into the soil with the end 58 pointed down. In an embodiment, the electrode structures 40, 42 have a top portion that is configured to facilitate placement of the corresponding electrodes 50, 52 at a desired depth within the soil. However, it is understood that the electrodes can have any orientation within the soil.

Each of the electrodes 50, 53, 54A, 54B can be fabricated from any suitable conductive material, such as copper, aluminum, and/or the like. The pointed end 58 can be fabricated of a rugged material, such as steel, to facilitate insertion into the soil. The remaining structure of each electrode structure 40, 42 can be formed of any suitable non-conductive material, such as plastic, rubber, and/or the like. Regardless, the structure of each component of the electrode structures 40, 42 can be configured to withstand the forces required to insert the electrode structures 40, 42 into the soil.

Figure 4:
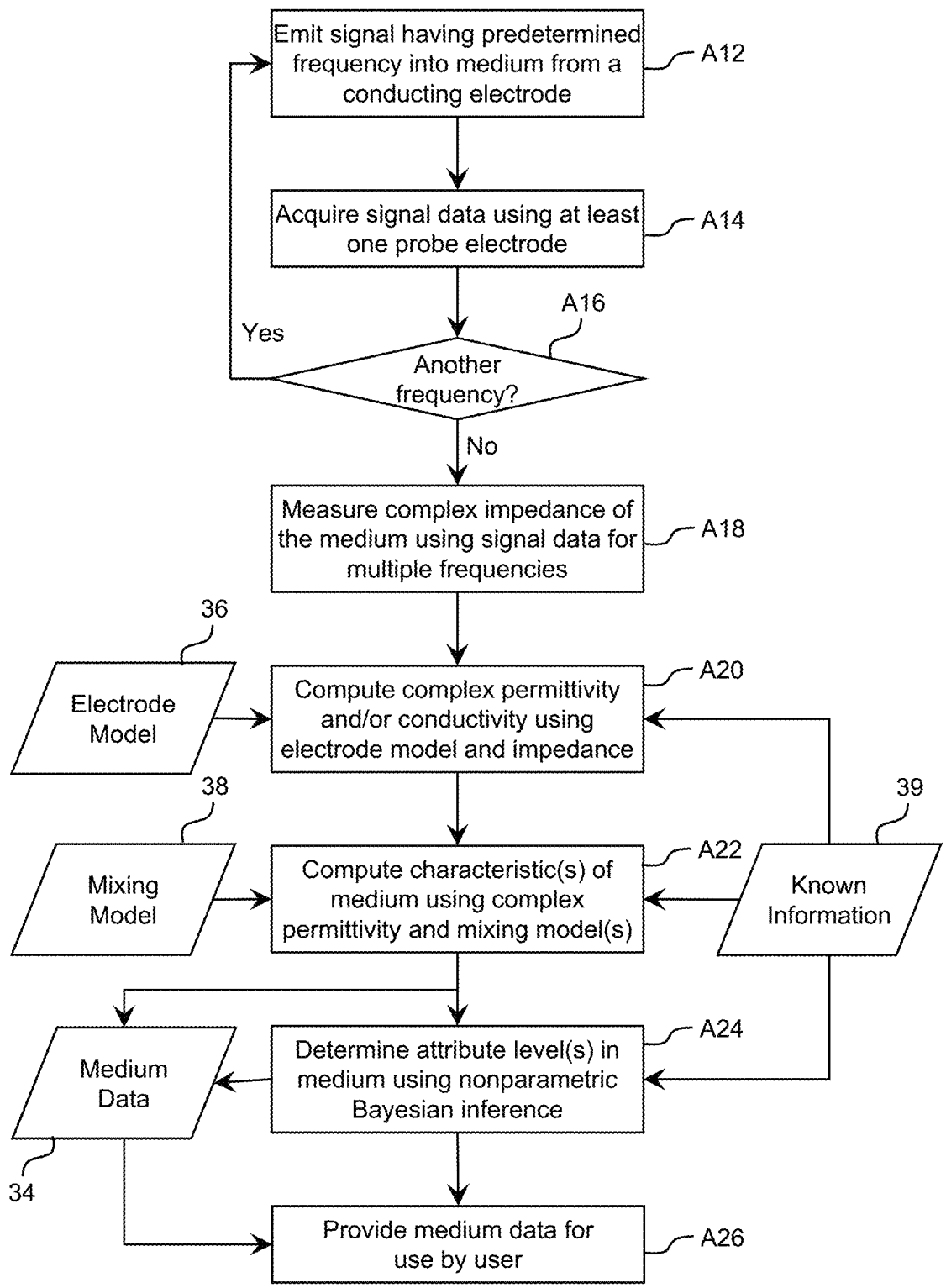
FIG. 4 shows an illustrative process for measuring one or more attributes of a medium according to an embodiment.

FIG. 4 shows an illustrative process for measuring one or more attributes of a medium, such as soil 4, which can be implemented by the environment 10. Referring to FIGS. 1-4, the user 12 can position and/or configure the electrode component 14 in a desired location within the soil 4 using any solution. For example, as discussed herein, the user 12 can insert the electrodes into the soil 4 individually (e.g., using a template) or collectively. Additionally, the user 12 can place soil 4 around the electrode component 14, e.g., in a container, in a hole in the ground 2, and/or the like.

In an embodiment, the environment 10 can provide an analysis solution that is self-calibrating. For example, the computer system 20 can be configured to self-determine what electrode pattern(s) and/or placement(s) are necessary to obtain the most accurate soil measurements for use in the soil models. To self-calibrate, the computer system 20 can use prior knowledge regarding the soil 2, which can be acquired from the user 12, from an external data source 33, such as the USDA soil survey app (e.g., soil texture, parent material information), from an external lab, and/or the like. In an embodiment, the computer system 20 can acquire a set of initial impedance measurements after placement of the electrode component 14 in the soil 4 to determine which of the active electrodes in the electrode component 14 will be used to take the measurements. Within the initial data set taken for the self-calibration process, the computer system 20 can analyze various data attributes, such as the signal-to-noise ratio, minimum resolution, and/or the like. As long as the measurements meet the model(s) requirements, the active electrode configuration(s) can be utilized. If the computer system 20 determines that none of the electrode patterns provides information that is useful for the models, the computer system 20 can prompt the user 12 to change the placement of the electrode component 14 in the soil 4, the electrode configuration for the electrode component 14, and/or the like.

Once positioned at a desired location and in a configuration suitable for acquiring measurement data of sufficient quality, the computer system 20 can emit electrical signals from the conducting electrode structure 40, which are subsequently detected by one or more of the probe electrode structures 42A-42D after traveling through the soil 4. To this extent, in action A12, the computer system 20 can emit an electrical signal having a predetermined frequency into the soil 4 from the conducting electrode 50 and in action A14, the computer system 20 can acquire electrical signal data using one or more of the probe electrodes 52 corresponding to the electrical signal after having traveled through and interacted with the soil 4. The electrical signal data can include, for example, a voltage magnitude and phase, a current magnitude and phase, etc., for the corresponding frequency. Additionally, the computer system 20 can store data corresponding to one or more electrical properties of the electrode component 14 which are not dependent on the electrical signals, such as resistance. In action A16, the computer system 20 can determine whether the process requires another electrical signal to be transmitted at another frequency. If so, the process can return to action A12.

In an embodiment, the process includes generation of multiple electrical signals, each of a different frequency, over a range of frequencies. In an embodiment, the range of frequencies includes radio frequencies. The range of frequencies can be selected based on one or more known attributes of the soil, which can be provided by the user 12, acquired from an external data source 33, and/or the like. In a more particular embodiment, an illustrative process can generate and detect electrical signals of frequencies in a range between 10 kHz and 10 MHz. However, it is understood that lower frequencies as well as frequencies of 100 MHz or even higher may be suitable for certain applications. In an illustrative embodiment, the range of frequencies is between 40 Hz and 100 MHz. In a more particular illustrative process, the signals are generated at increments within the range of frequencies using a logarithmic sweep over the range of frequencies. The number of increments can vary, e.g., within a range between 50 to 250 increments. In a more particular embodiment, the total number of increments is in a range between 100 to 200. However, it is understood that these ranges for the frequencies and increments are only illustrative. In other embodiments, electrical signals of higher and/or lower frequencies can be utilized and different amounts of increments, which can be uniform or non-uniform throughout the range of frequencies can be used.

In action A18, the computer system 20 can measure a complex impedance of the soil 4 using the signal data acquired for the electrical signals of multiple frequencies. For example, the computer system 20 can use the voltage magnitude and phase acquired for each frequency of electrical signal to calculate a complex voltage for the frequency. The computer system 20 can use the complex voltage to calculate the complex impedance and a known measurement scheme (e.g., voltage divider).

In action A20, the computer system 20 can compute the complex permittivity (e.g., effective permittivity) of the soil 4 using the complex impedance as well as an electrode model 36. The electrode model 36 can be selected based on a particular configuration of electrodes used to acquire the data. For example, the electrode model 36 can comprise a transmission line model. In an illustrative embodiment, the computer system 20 uses an electrode model 36 that is based on a coaxial transmission line model for the electrode component 14 shown in FIGS. 2A and 2B. For example, the model can include the formula:

$$C = \frac{\pi \varepsilon}{\ln\left(\frac{b}{a}\right)},$$

where C is the capacitance of the soil, ε is the permittivity of the soil, a is the radius of the wire (e.g., electrodes), and b is the radius between wires (e.g., between the conducting electrode 50 and probe electrode 52). However, it is understood that a coaxial transmission line model is only illustrative and other transmission line models, such as two-wire, planar, coplanar, etc., can be utilized. Adjustments to the model can be made based on the number of electrodes used in an active measurement (e.g., 2, 3, 4, or all 5) and their corresponding lengths. In particular, as the number of electrodes and their corresponding configuration changes, the computer system 20 can adjust different values within the model. In an embodiment, the electrode model 36 can further include a resistance-to-conductivity formula, which the computer system 20 can resolve to determine conductivity.

Regardless, the computer system 20 can use the electrode model 36 to calculate the complex permittivity (or complex conductivity) of the soil 4. For example, the measured complex impedance is dependent on a configuration of electrodes in the electrode component 14 and complex permittivity (or complex conductivity) properties of the soil 4. The electrode model 36 is a mathematical representation of the configuration of electrodes in the electrode component 14. The computer system 20 can use the electrode model 36 to remove an effect of the electrode configuration from the complex impedance, which yields the complex permittivity (or complex conductivity) properties of the soil 4. Therefore, other models can operate independently of the selected electrode configuration (setup). For example, if the electrode configuration should need to be modified (e.g., to fit a certain field or a laboratory application), the electrode model changes can be incorporated without the need to adjust or make changes to other aspects of the system (e.g., other models).

In an embodiment, the computer system 20 can measure a complex electrical conductivity of the soil 4. For example, the computer system 20 can determine the conductivity of the soil 4 by the phases (air, water, and solid particles) within a measured volume of the soil, which contribute to the measured conductivity. A measured effective conductivity of the soil 4 can be largely influenced by the water content and the conductivity of the soil solution (water), since both the air and solid particle phases are non-conducting ($\sigma$air=0, $\sigma$solid=0). While air and solid particles are non-conducting, they can influence the measurement due to their configuration (e.g., aggregation-porosity, connected pore space, structure, etc.) within the volume of soil 4.

In addition, the solid particles' shape, orientation and size distribution, cation exchange capacity (CEC) and wettability affect the effective conductivity. Tortuosity is used to describe the relationship of the pore space (water and air phases) on the effective conductivity measurement and can affect the effective conductivity. Components of the soil mixture, such as the specific surface area and particle shape, ionic strength and composition of the rock/soil contribute to the measured conductivity. The computer system 20 can incorporate particle shape (e.g., spherical sand grains to needle-like clay tactoids) into the effective conductivity modeling by using a depolarization factor, which describes the extent to which the inclusion of polarization is reduced according to its shape and orientation with respect to an applied electrical field. While the factors affecting the effective conductivity of a soil mixture do not act separately, the geometrical and interfacial effects are greatly influenced by the water content.

In an embodiment, the computer system 20 uses a conductivity model to interpret the measured signals. Illustrative conductivity models that can be used by the computer system 20 include: Archie's law; mean field theories (e.g., mixing formulas such as Maxwell formula/Maxwell-Garnett equation, Bruggeman's model, coherent potential approximation, and a universal mixing law), a self-similar model, which uses the effective medium theory (Maxwell-Garnett) and Archie's law to model pore space; Hilhorst model; the effective conductivity as two conductors in parallel; a model based on the low-frequency polarization of the Stern layer and the effect on the rest of the frequency data; methods/models that use the Maxwell-Wagner polarization (e.g., Maxwell-Wagner-Brugermann-Hanai (MWBH)); etc.

In an embodiment, the computer system 20 uses known information 39 regarding the soil 4 in order to select a corresponding conductivity model. For example, the known information 39 can include one or more known and/or unknown conditions and/or properties of a desired characteristic of the soil 4 to be determined. For example, the computer system 20 can use Archie's Law for soil 4 with low clay content and the self-similar model, due to its flexibility for simplification, when very little is known about the soil 4 and bulk properties of the soil solution are desired. The computer system 20 also can use the self-similar model in instances when the soil 4 has a broad particle size distribution, and thus a relatively low porosity and/or with non-spherical particles by averaging the depolarization factor over all possible particle orientations. The computer system 20 can obtain data corresponding to the known and/or unknown conditions from a user 12 and/or an external data source 33 using any solution.

In action A22, the computer system 20 can compute one or more characteristics of the soil 4 using the complex permittivity (or complex conductivity) and one or more mixing models 38. Illustrative characteristics of the soil 4 include the water content (e.g., volumetric moisture content), a level of compaction (e.g., density), pore water conductivity, soil salinity, porosity, nitrate level, etc. Each mixing model 38 can correspond to one or more characteristics of the soil 4. The computer system 20 can use the mixing model 38 to estimate content from the measured permittivity of the soil 4. Depending on the particular characteristic(s) to be computed, the computer system 20 can use the corresponding mixing model(s) 38 that provide an estimate for the characteristic(s). In an embodiment, the computer system 20 can use known information 39 regarding the soil 4 to select from multiple possible mixing models 38 for a particular characteristic. For example, the computer system 20 can use known data regarding the texture of the soil 4 to obtain an initial estimate of the porosity of the soil. The estimated porosity can be applied to a mixing model 38 to develop a density estimate as porosity is dependent on both texture and density.

In an embodiment, one or more of the mixing models 38 comprises a dielectric mixing model. In a more particular embodiment, the dielectric mixing model is similar to the Maxwell-Garnett (M-G) mixing model. The M-G mixing model is based on the volumetric fractions of the components within the volume of soil 4, not interaction effects between grains. The M-G two-phase mixing model is:

$$\varepsilon_{eff} = \varepsilon_b + 3f\varepsilon_b\left(\frac{\varepsilon_1 - \varepsilon_b}{\varepsilon_1 + 2\varepsilon_b - f(\varepsilon_1 - \varepsilon_b)}\right),$$

where $\varepsilon_b$ is the permittivity of the background material (e.g., air, water, and/or the like), $\varepsilon_1$ is the permittivity solid inclusion, f is the volume faction of $\varepsilon_1$ and $f=1-\phi$, $\phi$ is the porosity of the soil, and $\varepsilon_{eff}$ is the effective permittivity of the soil mixture. This macroscopic generalized mixing formula assumes the inclusion material is ellipsoid in shape and the sizes of the inclusions in the mixture do not exceed a tenth of the wavelength in the effective medium.

However, it is understood that the M-G mixing model is only one type of mixing model that can be utilized. For example, other mixing models can be selected when the soil 4 has a high dielectric contrast ratio (e.g., $\varepsilon_b:\varepsilon_1$), in which case the M-G mixing model has been shown to be less accurate. Other mixing models that use volume fractions and permittivities include the Bruggeman model, and the Lichtenecker model. Another mixing model is a Maxwell-Wagner (MW) model, which models the MW effect. The MW effect is an interfacial dispersion that occurs in mixtures with different permittivities. The MW effect typically occurs in the kHz to MHz region and is strongly dependent on conductivity of the mixture, the water's phase (bound or free water), and the temperature.

In an embodiment, the computer system 20 uses a mixing model 38 that determines the ionic concentrations of ions having differing conductivity at different frequencies from the conductivity measurements acquired for different frequencies. The mixing model 38 can use weighted averages of conductivities of the ions. For instance, assuming the soil 4 contains strong electrolytes at a low concentration (c<10 mM), then a molar conductivity follows Kohlrausch's law, $\Lambda_m=\Lambda_m^0-K\sqrt{c}$, such that K is an empirical constant that depends on the stoichiometry of the ions in solution, and $\Lambda_m^0$ is the limiting molar conductivity and is a known constant for common inorganic ions, e.g., $NO_3\Lambda_m^0=71.4$ cm$^2$/mol. The mixing model 38 can further use the Debye-Huckel-Onsager equation: $\Lambda_m=\Lambda_m^0-(A+B\Lambda_m^0)\sqrt{c}$, where A and B are constants that depend on temperature, charges of ions, dielectric constant and viscosity of solvent. In an embodiment, the computer system 20 can use these equations along with the measured MW conductivity frequency response to isolate the types and concentrations of different ions present in the soil 4.

In action A24, the computer system 20 can determine one or more attribute levels in the soil 4 from the characteristic (s) of the soil 4. For example, the computer system 20 can determine a nitrate level in the soil 4. In an embodiment, the computer system 20 uses a nonparametric Bayesian inference approach to determine one or more of the attribute levels (e.g., the nitrate level) in the soil 4. A general Bayesian approach has three components: the prior, the likelihood, and the posterior distributions. The prior can be described as what is known about the soil 4 before data is observed. The likelihood is the observed data. The posterior is what is known after the data is observed (e.g., nitrate level).

To this extent, the computer system 20 can implement a Bayesian solution to calculate the nitrate level. The computer system 20 can interpret data acquired for the soil 4 using the determined set of characteristics (e.g., water content, level of compaction, pore water conductivity, etc.) and additional known information 39 (e.g., priors) regarding the soil 4 to aid in calculating the nitrate level. For example, such known information 39 can include soil and environmental conditions. Illustrative known information 39 for the soil 4 can include a mineralogy, texture (e.g., particle sizes) which can provide an estimate for porosity, specific surface area, specific gravities of chief materials, etc. Illustrative known information for the environmental conditions include soil temperature, recent rainfall level, and/or the like. The computer system 20 can obtain the known information 39 from the user 12 and/or an external data source 33 using any solution. Additionally, the computer system 20 can use the resulting posterior distribution findings (e.g., previous nitrate prediction or a known nitrate level) as a prior distribution in the next test of the soil 4.

Use of a Bayesian solution provides the computer system 20 with versatility in the nitrate model such that the posterior's estimate of the nitrate level does not need to take a predetermined form. Instead, the computer system 20 can construct the estimate of the nitrate level according to information derived from the data and known information 39. The Bayesian approach provides a framework for the computer system 20 to select a model for the nitrate level and the nonparametric model allows for adaptation to changing data requirements. To this extent, the computer system 20 can adapt a complexity of the model (e.g., number of dimensions) to the data and can grow the complexity of the model with data size. In an embodiment, the computer system 20 can select a finite subset of dimensions depending on the data and marginalize out the unneeded dimensions over the prior. In particular, the computer system 20 can construct a likelihood function based on the observed field data and the nonparametric model.

It is understood that the nitrate level is only an illustrative attribute level in the soil that can be analyzed using a system described herein. Other illustrative attributes for which a level can be determined can include, without limitation, one or more of: potassium, phosphorous, calcium, magnesium, sodium, salinity, moisture, density, and/or the like. Additionally, embodiments can be utilized to analyze soil directed to other applications including, without limitation, soil contamination, quality control in food production, lawn care, and/or the like.

The computer system 20 can store various data generated during the process described herein as medium data 34. For example, the medium data 34 can include data corresponding to the characteristic(s) and/or attribute level(s) of the medium determined using the process described herein. Additionally, the medium data 34 can include data corresponding to the test, such as a time stamp, geographic location, and/or the like, as well as some or all of the known information 39 used in analyzing the medium. Still further, the computer system 20 can store the raw signal data acquired, data corresponding to a configuration of the electrodes used, data corresponding to the model(s) 36, 38 selected and used in the calculations, a version number for the model(s) and/or algorithm used, and/or the like. In this manner, the computer system 20 can store sufficient medium data 34 to recreate the analysis and/or apply revised analysis for the soil 4.

In action A26, the computer system 20 can provide one or more of the determined characteristics, attribute levels, and/or the like, of the soil 4 for use by the user 12. For example, the computer system 20 can display a density, moisture content, nitrate level, and/or the like, of the soil 4 as determined from the signal data. Additionally, the computer system 20 can transmit such data for use by another computer system, such as a soil management system, which can initiate one or more actions using the data (e.g., schedule an additional fertilization). Furthermore, the computer system 20 can store some or all of the data as soil data 34, which can be utilized as known information 39 for a subsequent evaluation of soil 4 for the same general location.

While shown and described herein primarily as a method and system for analyzing soil, it is understood that aspects of the invention further provide various alternative embodiments. For example, in one embodiment, the invention provides a computer program fixed in at least one computer-readable medium, which when executed, enables a computer system to analyze a medium. To this extent, the computer-readable medium includes program code, such as the analysis program 30 (FIG. 1), which enables a computer system to implement some or all of a process described herein. It is understood that the term "computer-readable medium" comprises one or more of any type of tangible medium of expression, now known or later developed, from which a copy of the program code can be perceived, reproduced, or otherwise communicated by a computing device. For example, the computer-readable medium can comprise: one or more portable storage articles of manufacture; one or more memory/storage components of a computing device; and/or the like.

In another embodiment, the invention provides a method of providing a copy of program code, such as the analysis program 30 (FIG. 1), which enables a computer system to implement some or all of a process described herein. In this case, a computer system can process a copy of the program code to generate and transmit, for reception at a second, distinct location, a set of data signals that has one or more of its characteristics set and/or changed in such a manner as to encode a copy of the program code in the set of data signals. Similarly, an embodiment of the invention provides a method of acquiring a copy of the program code, which includes a computer system receiving the set of data signals described herein, and translating the set of data signals into a copy of the computer program fixed in at least one computer-readable medium. In either case, the set of data signals can be transmitted/received using any type of communications link.

In still another embodiment, the invention provides a method of generating a system for analyzing a medium. In this case, the generating can include configuring a computer system, such as the computer system 20 (FIG. 1), to implement the method of analyzing a medium, such as a soil. The configuring can include obtaining (e.g., creating, maintaining, purchasing, modifying, using, making available, etc.) one or more hardware components, with or without one or more software modules, and setting up the components and/or modules to implement a process described herein. To this extent, the configuring can include deploying one or more components to the computer system, which can comprise one or more of: (1) installing program code on a computing device; (2) adding one or more computing and/or I/O devices to the computer system; (3) incorporating and/or modifying the computer system to enable it to perform a process described herein; and/or the like.

It is understood that, unless otherwise specified, each value is approximate and each range of values included herein is inclusive of the end values defining the range. As used herein, unless otherwise noted, the term "approximately" can be inclusive of values within +/−ten percent of the stated value, while the term "substantially" can be inclusive of values within +/−five percent of the stated value. Furthermore, the phrase "in real time" means that the task is completed within a short time duration for a human user. In an illustrative embodiment, "in real time" is inclusive of time periods less than ten minutes.

As used herein, unless otherwise noted, the term "set" means one or more (i.e., at least one) and the phrase "any solution" means any now known or later developed solution. The singular forms "a," "an," and "the" include the plural forms as well, unless the context clearly indicates otherwise. Additionally, the terms "comprises," "includes," "has," and related forms of each, when used in this specification, specify the presence of stated features, but do not preclude the presence or addition of one or more other features and/or groups thereof.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual in the art are included within the scope of the invention as defined by the accompanying claims.

What is claimed is:

1. A medium evaluation system, the system comprising:
a computer system including a processor configured for evaluating a medium, the evaluating including the processor:
   determining a level of at least one attribute of the medium, using signal data for the medium, the signal data including signal data acquired when each of a plurality of electrical signals traveled through the medium, wherein each of the plurality of electrical signals has a different frequency of a plurality of frequencies extending over a range of frequencies;
   wherein the determining includes computing a complex permittivity and/or a complex conductivity from the signal data; and
   wherein the determining uses a Bayesian inference solution to derive the level of at least one attribute of the medium from the complex permittivity and/or the complex conductivity and known information regarding the medium.

2. The system of claim 1, further comprising an electrode component including a conducting electrode and a probe electrode, wherein the processor is further configured to operate the electrode component to emit, from the conducting electrode, each of the plurality of electrical signals into the medium, and acquire, from the probe electrode, the signal data for the medium.

3. The system of claim 2, wherein the electrode component further includes a template or guide that enables a user to insert the electrodes into the medium at a known distance from each other.

4. The system of claim 3, wherein the template or guide enables selective insertion of the electrodes at one of a plurality of known distances.

5. The system of claim 2, wherein the processor is further configured to specify a configuration for placement of the electrodes in the medium based on the known information regarding the medium.

6. The system of claim 2, wherein the probe electrode includes a pair of guard electrodes located on opposing sides of a guarded electrode to eliminate electric field fringing effects at edges of the guarded electrode.

7. The system of claim 1, wherein the computing the complex permittivity and/or the complex conductivity includes:
   measuring a complex impedance of the medium using the signal data; and
   computing the complex permittivity and/or the complex conductivity, using the complex impedance and an electrode model corresponding to a configuration of electrodes used to acquire the signal data, wherein the electrode model removes an effect of an arrangement for the configuration of electrodes used to acquire the signal data from the complex impedance.

8. The system of claim 1, wherein the known information regarding the medium includes characteristics of the medium known from information available prior to each of the plurality of electrical signals traveling through the medium.

9. The system of claim 1, wherein the determining includes:
   computing a set of current characteristics of the medium using the complex permittivity and/or the complex conductivity; and
   determining a level of at least one attribute of the soil using the Bayesian inference solution applied to the set of current characteristics and the known information regarding the medium.

10. A portable medium evaluation system, the system comprising:
an electrode component including a conducting electrode and a probe electrode; and
a computer system including a processor configured for evaluating a medium, the evaluating including the processor:
   operating the electrode component to emit, from the conducting electrode, each of a plurality of electrical signals into the medium, wherein each of the plurality of electrical signals has a different frequency of a plurality of frequencies extending over a range of frequencies, and acquire, from the probe electrode, signal data for the medium, wherein the signal data is acquired when each of the plurality of electrical signals travels through the medium; and
   determining a level of at least one attribute of the medium, using the signal data for the medium, wherein the determining includes computing a complex permittivity and/or a complex conductivity from the signal data, and wherein the determining uses a Bayesian inference solution to derive the level of at least one attribute of the medium from the complex permittivity and/or the complex conductivity and known information regarding the medium.

11. The system of claim 10, wherein the electrode component further includes a template or guide that enables a user to insert the electrodes into the medium at a known distance from each other.

12. The system of claim 11, wherein the template or guide enables selective insertion of the electrodes at one of a plurality of known distances.

13. The system of claim 10, wherein the processor is further configured to specify a configuration for placement of the electrodes in the medium based on the known information regarding the medium.

14. The system of claim 10, wherein the probe electrode includes a pair of guard electrodes located on opposing sides of a guarded electrode to eliminate electric field fringing effects at edges of the guarded electrode.

15. The system of claim 10, wherein the medium is soil, and wherein the known information includes a water content of the medium and the at least one attribute level includes a nitrate level.

16. A method of evaluating a medium, the method comprising:
a computer system computing a complex permittivity and/or a complex conductivity, using signal data for the medium, the signal data including signal data acquired when each of a plurality of electrical signals traveled through the medium, wherein each of the plurality of electrical signals has a different frequency of a plurality of frequencies extending over a range of frequencies;
the computer system determining a level of at least one attribute of the medium, wherein the determining includes the computer system using a Bayesian inference solution to derive the level of at least one attribute of the medium from the complex permittivity and/or the complex conductivity and known information regarding the medium; and the computer system providing the level of the at least one attribute of the medium for use in evaluating the medium.

17. The method of claim 16, further comprising the computer system operating an electrode component to emit, from a conducting electrode, each of the plurality of electrical signals into the medium, and acquire, from a probe electrode, the signal data for the medium.

18. The method of claim 17, the computer system specifying a configuration for placement of the electrodes in the medium based on the set of known characteristics of the medium.

19. The method of claim 16, wherein the computer system computing the complex permittivity and/or the complex conductivity includes:

the computer system measuring a complex impedance of the medium using the signal data; and the computer system computing the complex permittivity and/or a complex conductivity, using the complex impedance and an electrode model corresponding to a configuration of the electrodes used to acquire the signal data, wherein the electrode model removes an effect of an arrangement for the electrode configuration used to acquire the signal data from the complex impedance.

20. The method of claim 16, wherein the computer system determining the level of the at least one attribute of the medium includes:

the computer system computing a set of current characteristics of the medium using the complex permittivity and/or the complex conductivity; and the computer system determining the level of the at least one attribute of the soil using the Bayesian inference solution applied to the set of current characteristics and the known information regarding the medium.

* * * * *